United States Patent
Fujii et al.

(10) Patent No.: US 10,429,306 B2
(45) Date of Patent: Oct. 1, 2019

(54) SURFACE PLASMON RESONANCE FLUORESCENCE ANALYSIS DEVICE AND SURFACE PLASMON RESONANCE FLUORESCENCE ANALYSIS METHOD

(71) Applicant: Konica Minolta, Inc., Tokyo (JP)

(72) Inventors: Hideyuki Fujii, Saitama (JP); Tetsuya Noda, Tokyo (JP); Koji Miyazaki, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 827 days.

(21) Appl. No.: 14/905,632

(22) PCT Filed: Jul. 17, 2014

(86) PCT No.: PCT/JP2014/003805
§ 371 (c)(1),
(2) Date: Jan. 15, 2016

(87) PCT Pub. No.: WO2015/008492
PCT Pub. Date: Jan. 22, 2015

(65) Prior Publication Data
US 2016/0153910 A1 Jun. 2, 2016

(30) Foreign Application Priority Data
Jul. 18, 2013 (JP) ................................. 2013-149311

(51) Int. Cl.
*G01N 21/64* (2006.01)
*G01N 33/543* (2006.01)
*G01N 21/552* (2014.01)

(52) U.S. Cl.
CPC ....... *G01N 21/648* (2013.01); *G01N 21/6428* (2013.01); *G01N 33/54373* (2013.01); *G01N 21/553* (2013.01); *G01N 2021/6439* (2013.01); *G01N 2021/6463* (2013.01)

(58) Field of Classification Search
None
See application file for complete search history.

(56) References Cited

U.S. PATENT DOCUMENTS

| | | | | |
|---|---|---|---|---|
| 7,030,989 B2 * | 4/2006 | Yager | ............ | G01N 21/553 356/445 |
| 2002/0182743 A1 | 12/2002 | Perkins | | |
| 2004/0181344 A1 * | 9/2004 | Stephanopoulos | ........ | G01N 33/5011 702/20 |
| 2008/0130004 A1 * | 6/2008 | Pyo | ........ | G01N 21/553 356/445 |
| 2009/0218499 A1 * | 9/2009 | Kimura | ......... | G01N 21/47 250/363.01 |
| 2009/0230308 A1 | 9/2009 | Kimura | | |
| 2009/0242802 A1 * | 10/2009 | Kimura | ........ | G01N 21/648 250/459.1 |
| 2009/0321661 A1 * | 12/2009 | Ohtsuka | ........ | G01N 21/05 250/459.1 |
| 2013/0078146 A1 | 3/2013 | Sando | | |

FOREIGN PATENT DOCUMENTS

| | | |
|---|---|---|
| JP | H10-170430 | 6/1998 |
| JP | 10-307141 A | 11/1998 |
| JP | 2009216532 A | 9/2009 |
| JP | 2009-244018 | 10/2009 |
| JP | 2012-098256 A | 5/2012 |
| WO | 2011152064 A1 | 12/2011 |
| WO | 2012042805 A1 | 4/2012 |
| WO | 2012172987 A1 | 12/2012 |

OTHER PUBLICATIONS

International Search Report dated Sep. 22, 2014 for PCT/JP2014/003805 and English translation.
Decision of Rejection dated Jul. 24, 2018 from corresponding Japanese Patent Application No. 2015-527183 and English translation.
Notice of Reasons for Rejection dated Dec. 26, 2017 from the corresponding Japanese Patent Application No. JP 2015-527183 and English translation.
Extended European Search Report dated Feb. 28, 2017 from the corresponding European Application No./Patent No. 14825688.6-1554 / 3023772 PCT/JP2014003805; Applicant: Konica Minolta,Inc.; Total of 10 pages.
Office Action dated Mar. 12, 2018 from the corresponding European Patent Application No. 14825688.6.

* cited by examiner

*Primary Examiner* — Ann Y Lam
(74) *Attorney, Agent, or Firm* — Lucas & Mercanti, LLP

(57) ABSTRACT

A surface plasmon resonance fluorescence analysis device has a chip holder for holding an analysis chip, a light source for irradiating excitation light, an angle adjustment unit for adjusting the angle of incidence of the excitation light in relation to the interface of a prism and metal film of the analysis chip, an excitation light reflection filter, a first optical sensor for detecting the fluorescence emitted from the analysis chip and transmitted through the excitation light reflection filter, a second optical sensor for detecting the plasmon scattered light emitted from the analysis chip and reflected by the excitation light reflection filter, and a control unit for controlling the angle adjustment unit. The control unit determines an enhancement angle on the basis of the plasmon scattered light detection results of the second optical sensor.

13 Claims, 4 Drawing Sheets

SURFACE PLASMON RESONANCE FLUORESCENCE ANALYSIS DEVICE AND SURFACE PLASMON RESONANCE FLUORESCENCE ANALYSIS METHOD

CROSS REFERENCE TO RELATED APPLICATION

This Application is a 371 of PCT/JP2014/003805 filed on Jul. 17, 2014 which, in turn, claimed the priority of Japanese Patent Application No. JP2013-149311 filed Jul. 18, 2013, both applications are incorporated herein by reference.

TECHNICAL FIELD

The present invention relates to a surface plasmon resonance fluorescence analysis device and a surface plasmon resonance fluorescence analysis method in which a substance to be detected contained in a sample is detected by utilizing surface plasmon resonance (SPR).

BACKGROUND ART

Highly sensitive and quantitative detection of a minute amount of a substance to be detected such as protein and DNA in laboratory tests makes it possible to perform treatment by quickly determining the patient's condition. In view of this, the analysis method and the analysis device which can quantitatively detect a minute amount of a substance to be detected with high sensitivity are demanded.

Surface plasmon-field enhanced fluorescence spectroscopy (hereinafter abbreviated as "SPFS") is known as a method which can detect a substance to be detected with high sensitivity (see, for example, PTLS 1 and 2).

PTLS 1 and 2 disclose an analysis method and an analysis device that utilize SPFS. In the analysis method and the analysis device, a sensor chip including a prism formed of a dielectric, a metal film formed on one surface of the prism, a capturing body (for example antibody) fixed on the metal film is used. When a sample containing a substance to be detected is provided on the metal film, the substance to be detected is captured by the capturing body (primary reaction). The substance to be detected thus captured is further labeled by a fluorescence material (secondary reaction). In this state, when the prism is irradiated with excitation light through the metal film at an angle at which surface plasmon resonance is caused, localized-field light can be generated on the surface of the metal film. With this localized-field light, the fluorescence material for labelling the captured substance to be detected on the metal film is selectively excited, and fluorescence emitted from the fluorescence material is observed. In the analysis method and the analysis device, the fluorescence is detected to detect the presence or the amount of the substance to be detected.

In such analysis methods and analysis devices utilizing SPFS, it is necessary to use highly sensitive light sensors such as a photomultiplier tube (PMT) and an avalanche photodiode (APD) to quantitatively detect weak fluorescence. An excitation light cutting filter that blocks excitation light and allows fluorescence to transmit therethrough is provided on the front of the light sensors.

CITATION LIST

Patent Literature

PTL 1
Japanese Patent Application Laid-Open No. 10-307141
PTL 2
WO2012/042805

SUMMARY OF INVENTION

Technical Problem

In analysis methods and analysis devices utilizing SPFS, it is necessary to set the incident angle of the excitation light with respect to the metal film such that the fluorescence intensity is maximized to sufficiently improve the detection sensitivity and the detection accuracy.

Regarding this point, PTL 1 discloses a configuration in which excitation light is emitted at an incident angle at which the intensity of reflection light from the metal film is minimized (hereinafter referred to as "resonance angle"). However, since the incident angle at which the intensity of fluorescence light is maximized and the resonance angle are slightly different from each other, the analysis method and the analysis device disclosed in PTL 1 have a room for improvement in detection sensitivity and detection accuracy.

In the analysis method and the analysis device disclosed in PTL 2, excitation light is emitted at an incident angle (hereinafter referred to as "reinforcement angle") at which the intensity of diffusing light generated by surface plasmon resonance (hereinafter referred to as "plasmon scattering light") is maximized. Since the reinforcement angle is closer to the incident angle at which the intensity of the fluorescence light is maximized than the resonance angle, the analysis method and the analysis device disclosed in PTL 2 are more advantageous than the analysis method and the analysis device disclosed in PTL 1 in terms of detection sensitivity and detection accuracy. However, in the analysis method and the analysis device disclosed in PTL 2, the plasmon scattering light is also detected with use of the light sensor for detecting fluorescence, and consequently a problem that the excitation light cutting filter has to be moved out from the light path of the light reception optical system at the time of determining the reinforcement angle.

An object of the present invention is to provide a surface plasmon resonance fluorescence analysis device and a surface plasmon resonance fluorescence analysis method which can determine the reinforcement angle at which the plasmon scattering light is maximized without moving out the excitation light cutting filter from the light path of the light reception optical system.

Solution to Problem

To achieve the above-mentioned object, a surface plasmon resonance fluorescence analysis device according to an embodiment of the present invention to which an analysis chip including a prism having a metal film provided on one surface of the prism is attached, and in which the metal film is irradiated with excitation light through the prism to excite a fluorescence material for labelling a substance to be detected on the metal film and fluorescence emitted from the fluorescence material is detected to detect presence or an amount of the substance to be detected, includes: a chip holder configured to detachably hold the analysis chip; a light source configured to emit excitation light; an angle adjusting section configured to adjust an incident angle of the excitation light with respect to the metal film to irradiate the metal film with the excitation light through the prism at a predetermined incident angle; a first light sensor configured to detect fluorescence emitted from the fluorescence material; a light reception optical system configured to guide light emitted from the metal film to the first light sensor; an excitation light reflection filter disposed in the light reception optical system, and configured to reflect light having a wavelength same as that of the excitation light emitted from the light source in the light emitted from the metal film; a second light sensor configured to detect the light reflected by the excitation light reflection filter; and a control section configured to control the angle adjusting section; wherein the control section controls the incident angle of the excitation light with respect to the metal film to be adjusted by the angle adjusting section on a basis of a detection result of the light obtained by the second light sensor.

In addition, to achieve the above-mentioned object, a surface plasmon resonance fluorescence analysis method according to an embodiment of the present invention in which fluorescence which is emitted by a fluorescence material for labelling a substance to be detected when the fluorescence material is excited by localized-field light based on surface plasmon resonance is detected to detect presence or an amount of the substance to be detected, includes: determining a reinforcement angle which is an incident angle at which an intensity of plasmon scattering light emitted from a metal film and reflected by an excitation light reflection filter is maximized, by irradiating the metal film with excitation light through a prism while changing an incident angle with respect to the metal film, and by detecting an intensity of the plasmon scattering light, the metal film being provided on one surface of the prism; placing a substance to be detected which is labeled by a fluorescence material on the metal film; and detecting an intensity of fluorescence light which is emitted from the fluorescence material for labelling the substance to be detected, and transmitted through the excitation light reflection filter, by irradiating the metal film with the excitation light through the prism such that the incident angle with respect to the metal film is the reinforcement angle.

Advantageous Effects of Invention

According to the present invention, during detection of a substance to be detected with use of SPFS, the reinforcement angle at which the plasmon scattering light is maximized can be determined without moving out the excitation light cutting filter (excitation light reflection filter) from the light path of the light reception optical system. Therefore, according to the present invention, the presence or the amount of a substance to be detected can be detected with high sensitivity, high accuracy and high speed. Moreover, according to the present invention, downsizing and cost reduction of the surface plasmon resonance fluorescence analysis device can be achieved.

DESCRIPTION OF EMBODIMENTS

In the following, embodiments of the present invention are described in detail with reference to the accompanying drawings.

Embodiment 1

Configuration of Detection Device

First, a surface plasmon resonance fluorescence analysis device (hereinafter also referred to as "SPFS device") according to Embodiment 1 of the present invention is described.

An SPFS device is used in a state where an analysis chip having a prism formed of a dielectric and a metal film formed on one surface of the prism is attached to the device. When a sample containing a substance to be detected is provided on the metal film, the substance to be detected is captured by a capturing body. At this time, the substance to be detected may or may not be labeled by a fluorescence material. When the captured substance to be detected has not been labeled by the fluorescence material, the captured substance to be detected is further labeled by the fluorescence material. When, in this state, the metal film is irradiated with excitation light at an angle that causes surface plasmon resonance, localized-field light can be generated in the area in the vicinity of the metal film. With the localized-field light, a fluorescence material for labelling the substance to be detected which is captured on the metal film is selectively excited, and fluorescence emitted from the fluorescence material is observed. The SPFS device measures the light amount of the fluorescence to detect the presence or the amount of the substance to be detected.

Figure 1:
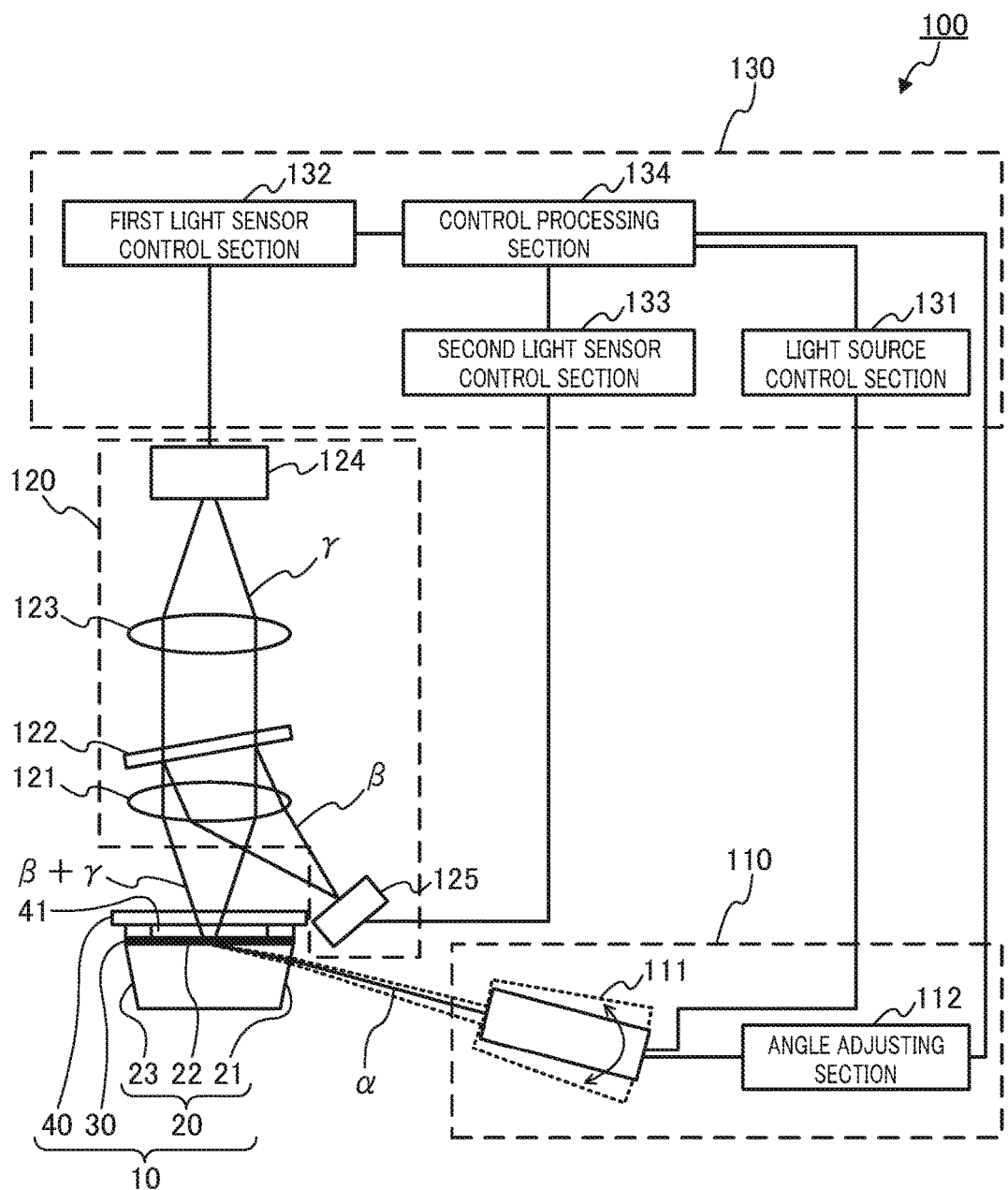
FIG. 1 is a schematic view illustrating a configuration of a surface plasmon resonance fluorescence analysis device according to Embodiment 1.
Figure 2:
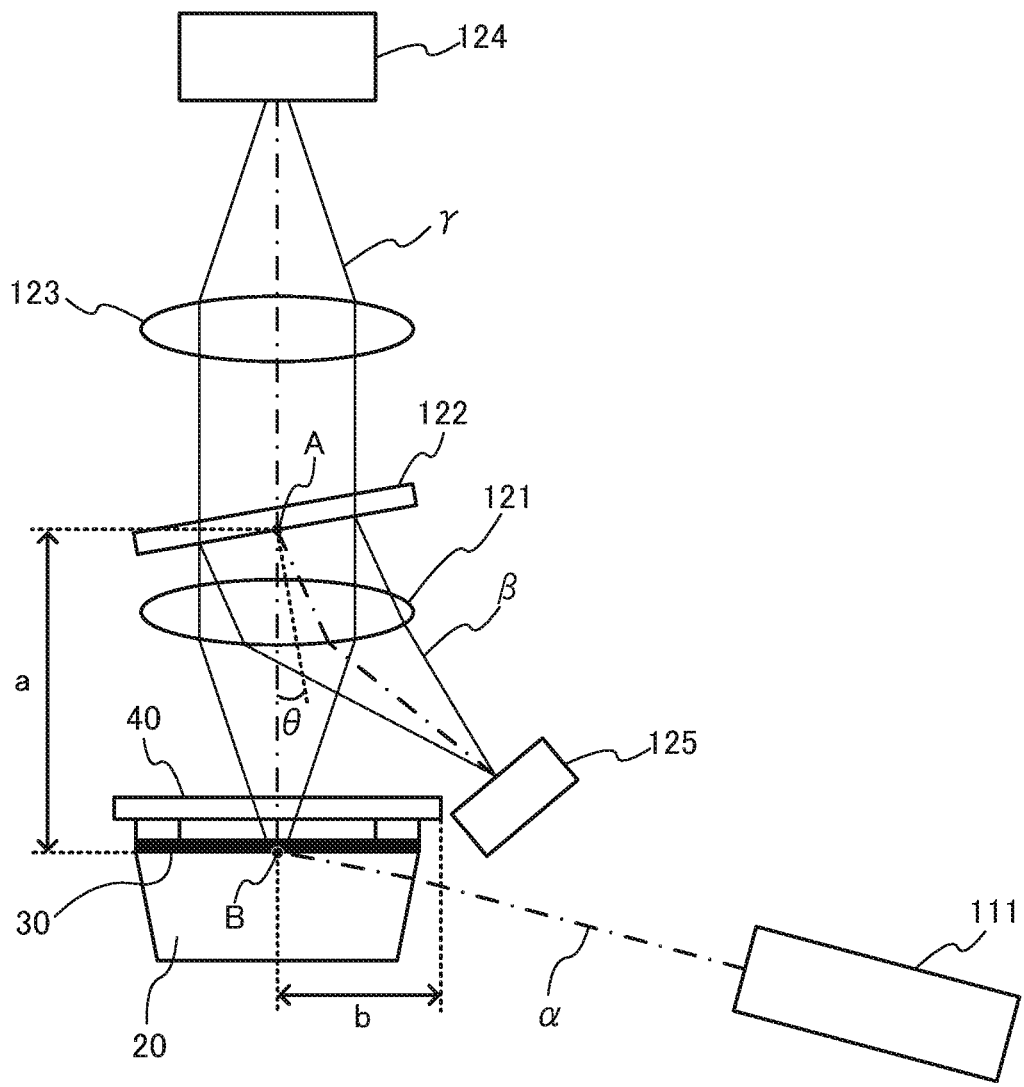
FIG. 2 is a partially enlarged schematic view of the device illustrated in FIG. 1.

FIG. 1 is a schematic view illustrating a configuration of SPFS device 100 according to Embodiment 1. FIG. 2 is a partially enlarged schematic view of SPFS device 100 illustrated in FIG. 1. As illustrated in FIG. 1, SPFS device 100 includes a chip holder (not shown in the drawing) for detachably holding analysis chip 10, excitation optical system unit 110 for irradiating analysis chip 10 with excitation light α, light reception optical system unit 120 for detecting light emitted from analysis chip 10 (plasmon scattering light β and fluorescence γ), and control section 130 for controlling the above-mentioned components. SPFS device 100 is used in a state where chip holder analysis chip 10 is attached to SPFS device 100. For such a configuration, analysis chip 10 is described first, and each component of SPFS device 100 is described after the description of analysis chip 10.

As illustrated in FIG. 1 and FIG. 2, analysis chip 10 includes prism 20 having incidence surface 21, film formation surface 22 and emission surface 23, metal film 30 formed on film formation surface 22, and channel closure 40 disposed on film formation surface 22 or metal film 30. Normally, analysis chip 10 is replaced for each analysis. Analysis chip 10 is preferably a structure with each side of several millimeters to several centimeters, but may be a smaller or larger structure which is not categorized as "chip."

Prism 20 is a dielectric which is transparent to excitation light α. Prism 20 includes incidence surface 21, film formation surface 22 and emission surface 23. Incidence surface 21 is a surface through which excitation light α from excitation optical system unit 110 enter prism 20. Metal film 30 is formed on film formation surface 22. Excitation light α having entered prism 20 is reflected by metal film 30. To be more specific, the excitation light α having entered prism 20 is reflected by the interface (film formation surface 22) between prism 20 and metal film 30. Emission surface 23 is a surface through which excitation light α reflected by metal film 30 is emitted out of prism 20. The shape of prism 20 is not limited. In the present embodiment, prism 20 has a columnar shape whose bottom surface is a trapezoid. The surface corresponding to a bottom side of the trapezoid is film formation surface 22. The surface corresponding to one of the legs is incidence surface 21, and the surface corresponding to the other of the legs is emission surface 23. Preferably, the trapezoid serving as the bottom surface is an isosceles trapezoid. In such a configuration, incidence surface 21 and emission surface 23 are symmetrical, and the S wave component of excitation light α does not easily remain in prism 20. Incidence surface 21 is formed such that excitation light α does not return to excitation optical system unit 110. The reason for this is that, if excitation light α returns to the laser diode serving as the excitation light source, the excitation state of the laser diode is disturbed, and the wavelength and the output of the excitation light α is varied. Therefore, the angle of incidence surface 21 is set within a scanning range around the ideal reinforcement angle such that that excitation light α does not perpendicularly incident on incidence surface 21. For example, the angle between incidence surface 21 and film formation surface 22, and the angle between film formation surface 22 and emission surface 23 are each approximately 80 degrees. Examples of the material of prism 20 include a resin and glass. Preferably, the material of prism 20 is a resin which has a refractive index of 1.4 to 1.6 and causes a small birefringence.

Metal film 30 is formed on film formation surface 22 of prism 20. When metal film 30 is provided, interaction (surface plasmon resonance) is caused between the photon of excitation light α which is incident on film formation surface 22 under the total reflection condition and the free electron in metal film 30, and thus localized-field light can be generated on the surface of metal film 30. The material of metal film 30 is not limited as long as surface plasmon resonance can be caused. Examples of the material of metal film 30 include gold, silver, copper, aluminum, and their alloys. In the present embodiment, metal film 30 is a thin film formed of gold. The formation method for metal film 30 is not limited. Examples of the formation method for metal film 30 include sputtering, deposition, and plating. Preferably, the thickness of metal film 30 is, but not limited to, 30 to 70 nm.

In addition, although not illustrated in FIG. 1 and FIG. 2, a capturing body for capturing the substance to be detected may be fixed on the surface of prism 20 that faces away from metal film 30. When a capturing body is fixed, the substance to be detected can be selectively detected. In the present embodiment, a capturing body is uniformly fixed in a predetermined region on metal film 30. The type of the capturing body is not limited as long as the substance to be detected can be captured. For example, the capturing body is an antibody or its fragments specific to the substance to be detected.

Channel closure 40 is disposed on the surface of metal film 30 that faces away from prism 20 with channel 41 interposed therebetween. When metal film 30 is partly formed on film formation surface 22 of prism 20, channel closure 40 may be disposed on film formation surface 22 with channel 41 interposed therebetween. Together with metal film 30 (and prism 20), channel closure 40 forms flow channel 41 through which liquid such as a sample, fluorescence labeling solution, and washing solution flows. The capturing body is exposed to the inside of channel 41. Both ends of channel 41 are respectively connected to the inlet and outlet (both omitted in the drawing) formed on the top surface of channel closure 40. When liquid is injected into channel 41, the liquid makes contact with the capturing body in channel 41. Channel closure 40 is formed of a material transparent to light (plasmon scattering light β and fluorescence γ) emitted from the surface of metal film 30 that faces away from prism 20 and from the area in the vicinity of the surface of metal film 30. Examples of the material of channel closure 40 include resin. As long as the above-mentioned light can be guided to light reception optical system unit 120, channel closure 40 may be partly formed of an opaque material. Channel closure 40 is joined to metal film 30 or prism 20 by bonding using a double-sided tape or an adhesive agent, laser welding, ultrasound welding, or pressure fixing using a clamping member, for example.

As illustrated in FIG. 1 and FIG. 2, excitation light α guided to prism 20 enters prism 20 from incidence surface 21. The excitation light α having entered prism 20 is incident on the interface (film formation surface 22) between prism 20 and metal film 30 at a total reflection angle (at an angle that causes surface plasmon resonance). The reflection light from the interface is emitted out of prism 20 from emission surface 23 (not shown in the drawing). Meanwhile, when excitation light α is incident on the interface at an angle that causes surface plasmon resonance, plasmon scattering light β and fluorescence γ are emitted from metal film 30 and the area in the vicinity of metal film 30 in the direction toward light reception optical system unit 120.

Next, the components of SPFS device 100 are described. As described above, SPFS device 100 includes a chip holder (not shown in the drawing), excitation optical system unit 110, light reception optical system unit 120 and control section 130.

The chip holder (not shown in the drawing) holds analysis chip 10 at a predetermined position. Analysis chip 10 is irradiated with excitation light α from excitation optical system unit 110 in the state where analysis chip 10 is held by the chip holder. At this time, plasmon scattering light β having a wavelength same as that of excitation light α, fluorescence γ output from the fluorescence material and the like are emitted upward from the surface of metal film 30 that faces away from prism 20 and from the area in the vicinity of the surface. In addition, excitation light α is reflected by the interface between prism 20 and metal film 30, and emitted to the outside of prism 20 (not shown in the drawing).

Excitation optical system unit 110 includes light source unit 111 that emits excitation light α, and angle adjusting section 112 that adjusts the incident angle of excitation light α with respect to the interface (film formation surface 22) between prism 20 and metal film 30.

Light source unit 111 includes a laser diode (hereinafter abbreviated as "LD") as an excitation light source, and emits excitation light α (single mode laser light) toward incidence surface 21 of analysis chip 10 held by the chip holder. To be more specific, light source unit 111 emits P wave with respect to the interface (film formation surface 22) between prism 20 and metal film 30 of analysis chip 10 toward incidence surface 21 such that the angle of excitation light α with respect to the interface is a total reflection angle. For example, light source unit 111 includes an LD unit, a first shaper and a shaping optical system (which are not shown in the drawing).

The LD unit emits collimated excitation light α having a constant wavelength and a constant light amount such that the irradiation spot on the interface (film formation surface 22) between prism 20 and metal film 30 has a substantially circular shape. The LD unit includes an LD as an excitation light source, a collimator that collimates excitation light α emitted from the LD, and a temperature adjusting circuit that adjusts the light amount of excitation light α to a constant value. The excitation light α emitted from the LD has a flat outline shape even after it is collimated. In view of this, the LD is held at a predetermined orientation, or a slit having a predetermined shape is inserted to a shaping optical system described later such that the irradiation spot on the interface (film formation surface 22) has a substantially circular shape. In addition, the wavelength and the light amount of excitation light α emitted from the LD vary depending on the temperature. In view of this, the temperature adjusting circuit monitors the light amount of the light diverged from the collimated excitation light α with use of a photodiode and the like, and adjusts the temperature of the LD such that the wavelength and the light amount of the excitation light α is adjusted to a constant value with use of a heater, a Peltier element and the like.

The first shaper includes a first band pass filter (hereinafter abbreviated as "BPF1") and a linear polarization filter (hereinafter abbreviated as "LP"), and shapes the excitation light α emitted from the LD unit. Since the excitation light α from the LD unit has a slight wavelength distribution width, BPF1 changes the excitation light α from the LD unit to narrowband light composed only of a center wavelength. In addition, since the excitation light α from the LD unit is not complete linear polarization, the LP changes the excitation light α from the LD unit to complete linear polarization light. The first shaper may include a half-wave plate that adjusts the polarization direction of excitation light α such that the P wave component is incident on metal film 30.

The shaping optical system adjusts the beam diameter, the outline shape and the like of excitation light α such that the irradiation spot on the interface (film formation surface 22) between prism 20 and metal film 30 has a circular shape of a predetermined size. The excitation light α emitted from the shaping optical system is applied to prism 20 of analysis chip 10. The shaping optical system is a slit, a zooming section, or the like, for example.

It is to be noted that the type of the light source included in light source unit 111 is not limited, and may not be the LD. Examples of the light source include a light-emitting diode, a mercury lamp, and other laser light sources. In the case where the light emitted from the light source is not a beam, the light emitted from the light source is converted to a beam by a lens, a mirror, a slit or the like. In addition, in the case where the light emitted from the light source is not monochromatic light, the light emitted from the light source is converted to monochromatic light by a diffraction grid or the like. Further, in the case where the light emitted from the light source is not linear polarization, the light emitted from the light source is converted to linear polarization light by a polarizer or the like.

Angle adjusting section 112 adjusts the incident angle of excitation light α to metal film 30 (the interface (film formation surface 22) between prism 20 and metal film 30). Angle adjusting section 112 relatively rotates the optical axis of excitation light α and the chip holder to apply excitation light α to a predetermined position of metal film 30 (film formation surface 22) through prism 20 at a predetermined incident angle. In the present embodiment, angle adjusting section 112 rotates light source unit 111 about the axis orthogonal to the optical axis of excitation light α. At this time, the position of the rotation axis is set such that the irradiation position on metal film 30 (film formation surface 22) is not substantially moved when the incident angle is scanned. For example, when the position of the rotation center is set at a position near the intersection of the optical axes of two rays of excitation light α at both ends of the scanning range of the incident angle (at a position between the irradiation position on film formation surface 22 and incidence surface 21), the shift of the irradiation position can be minimized.

Light reception optical system unit 120 is disposed to face the surface of metal film 30 facing away from prism 20 in analysis chip 10 held by the chip holder. To be more specific, light reception optical system unit 120 is disposed such that first lens 121, second lens 123 and first light sensor 124 described later are located at positions on a line that passes through the irradiation spot of excitation light α on metal film 30 (film formation surface 22) and is perpendicular to the surface of metal film 30. Light reception optical system unit 120 detects light emitted from metal film 30 (plasmon scattering light β and fluorescence γ). Light reception optical system unit 120 includes first lens 121, excitation light reflection filter 122, second lens 123, first light sensor 124 and second light sensor 125.

First lens 121 and second lens 123 make up a conjugate optical system that is not easily influenced by stray light. The light rays that travel between first lens 121 and second lens 123 are substantially parallel light. First lens 121 and second lens 123 bring fluorescence γ emitted from metal film 30 into an image on the light reception surface of first light sensor 124. In addition, together with excitation light reflection filter 122, first lens 121 condenses plasmon scattering light β emitted from metal film 30 (analysis chip 10) on the light reception surface of second light sensor 125 as described later.

Excitation light reflection filter 122 is disposed between first lens 121 and second lens 123. Excitation light reflection filter 122 reflects light having a wavelength of excitation light α (plasmon scattering light β) while allowing fluorescence γ to transmit therethrough so as to prevent light which does not have the wavelength of fluorescence γ from reaching first light sensor 124. That is, excitation light reflection filter 122 functions as "excitation light cutting filter" that removes a noise component from the light reaching first light sensor 124 and contributes to improvement the detection accuracy and the sensitivity for weak fluorescence γ.

As excitation light reflection filter 122, a transparent substrate whose one surface or both surfaces is coated with a dielectric multi-layer film may be adopted, for example. A dielectric multi-layer film can be formed by alternately laminating a layer made of a high refractive index material and a layer made of a low refractive index material. By appropriately setting the thickness and the number of the layers at the formation of the film, a filter having the desired transmission reflection characteristics can be obtained. Examples of the high refractive index material include oxides of Ti, Nb, Ta, La and the like (for example, $TiO_2$, $Nb_2O_5$, $Ta_2O_5$ and the like). Examples of the low refractive index material include oxides of Si, Al and the like (for example, $SiO_2$ and the like). For example, excitation light reflection filter 122 can be produced by alternately laminating a $Nb_2O_5$ layer (having a thickness of approximately 100 nm) and a $SiO_2$ layer (having a thickness of approximately 100 nm) until 40 to 50 layers are laminated on the surface of a glass substrate (BK7) to form a dielectric multi-layer film (having a thickness of 4000 to 5000 nm). In excitation light reflection filter 122 obtained in this manner, when the incident angle of a main light beam on a filter is 20 degrees, the reflectance of light having a wavelength of 635 to 645 nm is 99% or greater, and the reflectance of light having a wavelength of 665 to 675 nm is 1% or smaller.

As illustrated in FIG. 1 and FIG. 2, excitation light reflection filter 122 is disposed to be tilted with respect to the optical axis of the conjugate optical system (light reception optical system) composed of first lens 121 and second lens 123. Accordingly, plasmon scattering light β reflected by excitation light reflection filter 122 travels toward second light sensor 125 without returning to analysis chip 10.

Preferably, the inclination angle θ(°) of the perpendicular of excitation light reflection filter 122 with respect to the optical axis of the conjugate optical system (light reception optical system) illustrated in FIG. 2 satisfies the following Expression (1). With such a configuration, second light sensor 125 that detects plasmon scattering light β can be disposed at a position where second light sensor 125 does not interfere with analysis chip 10. It is to be noted that inclination angle θ greater than 45 degrees is not preferable since the transmittance of fluorescence γ is low when inclination angle θ is greater than 45 degrees.

$$\tfrac{1}{2}\tan^{-1}(b/a) < \theta \le 45 \qquad (1)$$

wherein "a" is a distance between intersection A of the optical axis of the conjugate optical system (light reception optical system) with excitation light reflection filter 122, and intersection B of the optical axis of the conjugate optical system (light reception optical system) with film formation surface 22 of prism 20; and "b" is the shortest distance to an end portion of analysis chip 10 from intersection B in the direction orthogonal to the optical axis of the conjugate optical system (light reception optical system) (see FIG. 2).

First light sensor 124 detects fluorescence γ emitted from metal film 30. For example, first light sensor 124 is a photomultiplier tube having a high sensitivity and a high S/N ratio. Alternatively, first light sensor 124 may be an avalanche photodiode (APD) or the like. It is to be noted that the size of the irradiation spot of excitation light α on one surface of metal film 30 (the surface facing away from prism 20) is adjusted to a size smaller than the size of the measurement region of first light sensor 124 on the other surface of metal film 30 (the surface facing away from first lens 121) (see FIG. 1). With such a configuration, it is possible to prevent the irradiation spot from being displaced from the measurement region even when the position of the irradiation spot is slightly shifted due to errors of parameters of prism 20.

Second light sensor 125 detects plasmon scattering light β emitted from metal film 30 (the surface of metal film 30 and the area in the vicinity of the surface). Second light sensor 125 is disposed at a position where plasmon scattering light β reflected by excitation light reflection filter 122 can be detected. In the present embodiment, second light sensor 125 is disposed at a position near the condensing point of plasmon scattering light β which is reflected by excitation light reflection filter 122 and condensed by first lens 121. With such a configuration in which plasmon scattering light β reflected by excitation light reflection filter 122 is condensed at first lens 121, it is possible to use a small-sized light sensor having a small light reception area, or a light sensor having a low sensitivity as second light sensor 125. As a matter of course, a light sensor having a high sensitivity may be used as second light sensor 125. For example, second light sensor 125 is a photomultiplier tube, an avalanche photodiode (APD), a commonly-used photodiode (PD) or the like.

Control section 130 unitarily performs control of driving sections, quantification of the light reception amount of first light sensor 124 and second light sensor 125 and the like. In the present embodiment, control section 130 includes light source control section 131 that controls light source unit 111, first light sensor control section 132 that controls first light sensor 124, second light sensor control section 133 that controls second light sensor 125, and control processing section 134. Control processing section 134 comprehensively controls angle adjusting section 112, light source control section 131, first light sensor control section 132 and second light sensor control section 133 so as to control the entire operation of SPFS device 100. Control section 130 is a computer for executing software for example. As described later, control section 130 (control processing section 134) controls the incident angle of excitation light α with respect to metal film 30 (film formation surface 22) at the time of fluorescence measurement on the basis of the measurement result of plasmon scattering light β obtained by second light sensor 125.

In addition, control section 130 (control processing section 134 and light source control section 131) controls light source unit 111 such that the light amount of excitation light α is different between the state where second light sensor 125 is detecting plasmon scattering light β to determine the incident angle of excitation light α with respect to metal film 30 (film formation surface 22), and the state where first light sensor 124 is detecting fluorescence γ to detect the substance to be detected. To be more specific, control section 130 controls light source unit 111 such that the light amount of excitation light α at the time when second light sensor 125 is detecting plasmon scattering light β is greater than the light amount of excitation light α at the time when first light sensor 124 is detecting fluorescence γ. With such a configuration of increasing the light amount of excitation light α at the time of detecting plasmon scattering light β (at the time of determining determination the reinforcement angle), it is possible to use an inexpensive light sensor having a lower detection sensitivity as second light sensor 125. Preferably, the light amount of excitation light α is not increased more than necessary at the time of detecting fluorescence γ in view of suppressing discoloration of the fluorescence material.

Figure 3:
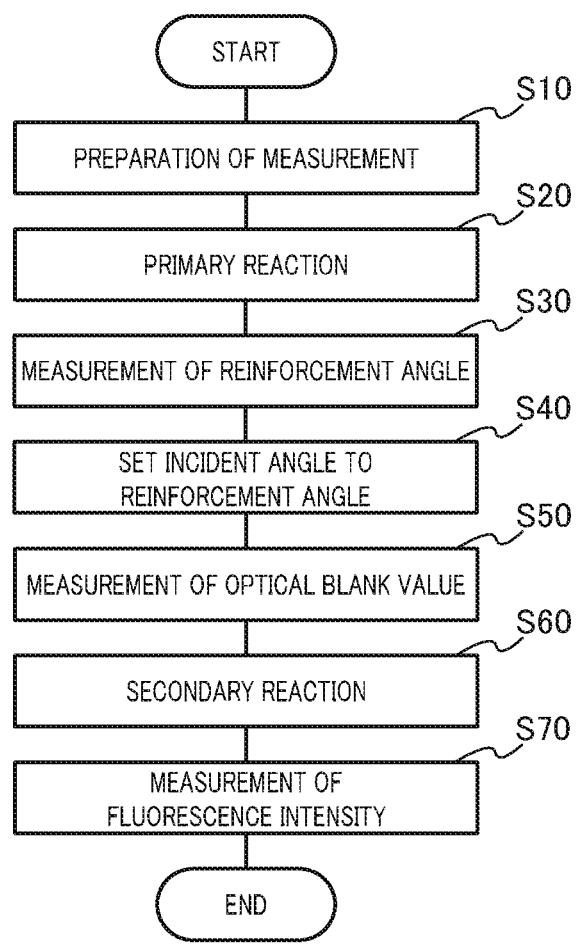
FIG. 3 is a flowchart of an exemplary operation procedure of the device illustrated in FIG. 1.

Next, the detection operation of SPFS device 100 is described. FIG. 3 is a flowchart of an exemplary operation procedure of SPFS device 100.

First, preparation for measurement is performed (step S10). To be more specific, analysis chip 10 is placed at a predetermined position of SPFS device 100. When a moisturizing agent presents in channel 41 of analysis chip 10, the inside of channel 41 is washed to remove the moisturizing agent so that the capturing body can appropriately capture the substance to be detected.

Next, a reaction between the substance to be detected in the sample and the capturing body is caused (primary reaction, step S20). To be more specific, the sample is injected into channel 41, and the sample and the capturing body are brought into contact with each other. When the substance to be detected presents in the sample, at least part of the substance to be detected is captured by the capturing body. Thereafter, the inside of channel 41 is washed with buffer solution or the like to remove materials which have not been captured by the capturing body. The kind of the sample is not limited. Examples of the sample include bodily fluids such as blood, serum, plasma, urine, nasal mucus, saliva, and semen, and their diluted solutions.

Next, while irradiating a predetermined area of metal film 30 (film formation surface 22) with excitation light α, the incident angle of excitation light α with respect to metal film 30 (film formation surface 22) is scanned, and an optimum incident angle is determined (step S30). To be more specific, control processing section 134 controls light source unit 111 and angle adjusting section 112 to scan the incident angle of excitation light α with respect to metal film 30 (film formation surface 22) while irradiating a predetermined area of metal film 30 (film formation surface 22) with excitation light α. Simultaneously, control processing section 134 controls second light sensor control section 133 such that second light sensor 125 detects plasmon scattering light β from metal film 30 (the surface of metal film 30 and the area in the vicinity of the surface). The plasmon scattering light β from metal film 30 (the surface of metal film 30 and the area in the vicinity of the surface) is collimated by first lens 121, and reaches excitation light reflection filter 122. The plasmon scattering light β is reflected by excitation light reflection filter 122, which is disposed to be tilted with respect to the central axis of first lens 121, and is obliquely incident on first lens 121. Thus, the plasmon scattering light β reaches second light sensor 125 without returning to metal film 30. Second light sensor 125 detects the intensity of the plasmon scattering light β which has been reflected by excitation light reflection filter 122 in the above-mentioned manner. In this manner, control processing section 134 obtains data containing a relationship between the incident angle of excitation light α and the intensity of plasmon scattering light β. Then, control processing section 134 analyzes the data by fitting such as quadratic approximation, and determines the incident angle (reinforcement angle) at which the intensity of the plasmon scattering light β is maximized. While the reinforcement angle is basically determined based on the material and the shape of prism 20, the thickness of metal film 30, the refractive index of the liquid in channel 41 and the like, the reinforcement angle is also slightly varied by various factors such as the kind and the amount of the fluorescence material in channel 41, and shaping errors of prism 20. In view of this, it is preferable to determine the reinforcement angle each time analysis is performed. The reinforcement angle is determined in the order of about 0.1 degree.

During measurement of the reinforcement angle (step S30), the light amount of excitation light α may be set at a value greater than that for measurement of the fluorescence intensity (step S70) that is performed afterward. As described above, with such a configuration, it is possible to use an inexpensive light sensor having a lower detection sensitivity as second light sensor 125. It is to be noted that, since no fluorescence material presents in channel 41 at this point of time, the problem of discoloration of the fluorescence material is not required to be considered.

Next, the incident angle of excitation light α with respect to metal film 30 (film formation surface 22) is set to the reinforcement angle determined at the preceding step (step S40). To be more specific, control processing section 134 controls angle adjusting section 112 to set the incident angle of excitation light α with respect to metal film 30 (film formation surface 22) to the reinforcement angle. In the following steps, the incident angle of excitation light α with respect to metal film 30 (film formation surface 22) is kept at the reinforcement angle.

Next, metal film 30 (film formation surface 22) is irradiated with excitation light α, and the intensity of light having a wavelength same as that of fluorescence γ (optical blank value) is measured (step S50). To be more specific, control processing section 134 controls light source control section 131 to emit excitation light α to light source unit 111. Simultaneously, control processing section 134 controls first light sensor control section 132 such that first light sensor 124 detects the intensity of light having a wavelength same as that of fluorescence γ. The measurement value is sent to control processing section 134 and recorded as an optical blank value.

Next, the substance to be detected that has been captured by the capturing body is labeled by a fluorescence material (secondary reaction, step S60). To be more specific, a fluorescence labeling solution is injected into channel 41. The fluorescence labeling solution is, for example, a buffer solution containing an antibody (secondary antibody) labeled by a fluorescence material. When the fluorescence labeling solution is injected into channel 41, the fluorescence labeling solution makes contact with the substance to be detected, and the substance to be detected is labeled by the fluorescence material. Thereafter, the inside of channel 41 is washed with buffer solution and the like to remove the free fluorescence material and the like.

Finally, metal film 30 (film formation surface 22) is irradiated with excitation light α and the intensity of fluorescence γ emitted from metal film 30 (the surface of metal film 30 and the area in the vicinity of the surface) is measured (step S70). To be more specific, control processing section 134 controls light source control section 131 to emit excitation light α to light source unit 111. Simultaneously, control processing section 134 controls first light sensor control section 132 such that first light sensor 124 detects fluorescence γ emitted from metal film 30 (metal film 30 and the area in the vicinity of metal film 30). Control processing section 134 subtracts the optical blank value from the measurement value to calculate a fluorescence intensity correlated with the amount of the substance to be detected. The fluorescence intensity is converted to the amount or the concentration of the substance to be detected and the like as necessary.

Through the above-mentioned procedures, it is possible to detect the presence of the substance to be detected or the amount of the substance to be detected in the sample without moving the excitation light cutting filter (excitation light reflection filter 122) from or to the light path of the light reception optical system.

As described above, in SPFS device 100 according to the present embodiment, the incident angle of excitation light α with respect to metal film 30 (film formation surface 22) is set to a reinforcement angle at which plasmon scattering light β is maximized to detect fluorescence γ at the time of detecting the substance to be detected. Accordingly, SPFS device 100 according to the present embodiment can detect the presence or the amount of the substance to be detected with high sensitivity and high accuracy.

In addition, with SPFS device 100 according to the present embodiment, it is not necessary to move out the excitation light cutting filter (excitation light reflection filter 122) from the light path of the light reception optical system even at the time of determining the optimum incident angle (reinforcement angle) of excitation light α with respect to metal film 30 (film formation surface 22). Accordingly, unlike the conventional SPFS device (see PTL 2), SPFS device 100 according to the present embodiment does not require the mechanism for switching the position of the excitation light cutting filter, and thus can achieve downsizing and cost reduction.

In the conventional SPFS device (see PTL 2), plasmon scattering light β and fluorescence γ are detected with use of the same light sensor, and therefore it is necessary to move the ND filter to the light path of the light reception optical system at the time of detecting plasmon scattering light β. In contrast, in SPFS device 100 according to the present embodiment, plasmon scattering light β and fluorescence γ are detected with use of respective different light sensors, and therefore it is not necessary to move the ND filter to the light path of the light reception optical system at the time of determining the optimum incident angle (reinforcement angle) of excitation light α with respect to metal film 22 (film formation surface 22). Also from this view point, SPFS device 100 according to the present embodiment can achieve downsizing and cost reduction.

Embodiment 2

As with SPFS device 100 according to Embodiment 1, SPFS device 200 according to Embodiment 2 includes a chip holder, excitation optical system unit 110, light reception optical system unit 220 and control section 130. SPFS device 200 according to Embodiment 2 is different from SPFS device 100 according to Embodiment 1 only in the configuration of light reception optical system unit 220. Therefore, in the present embodiment, only light reception optical system unit 220 is described.

Figure 4:
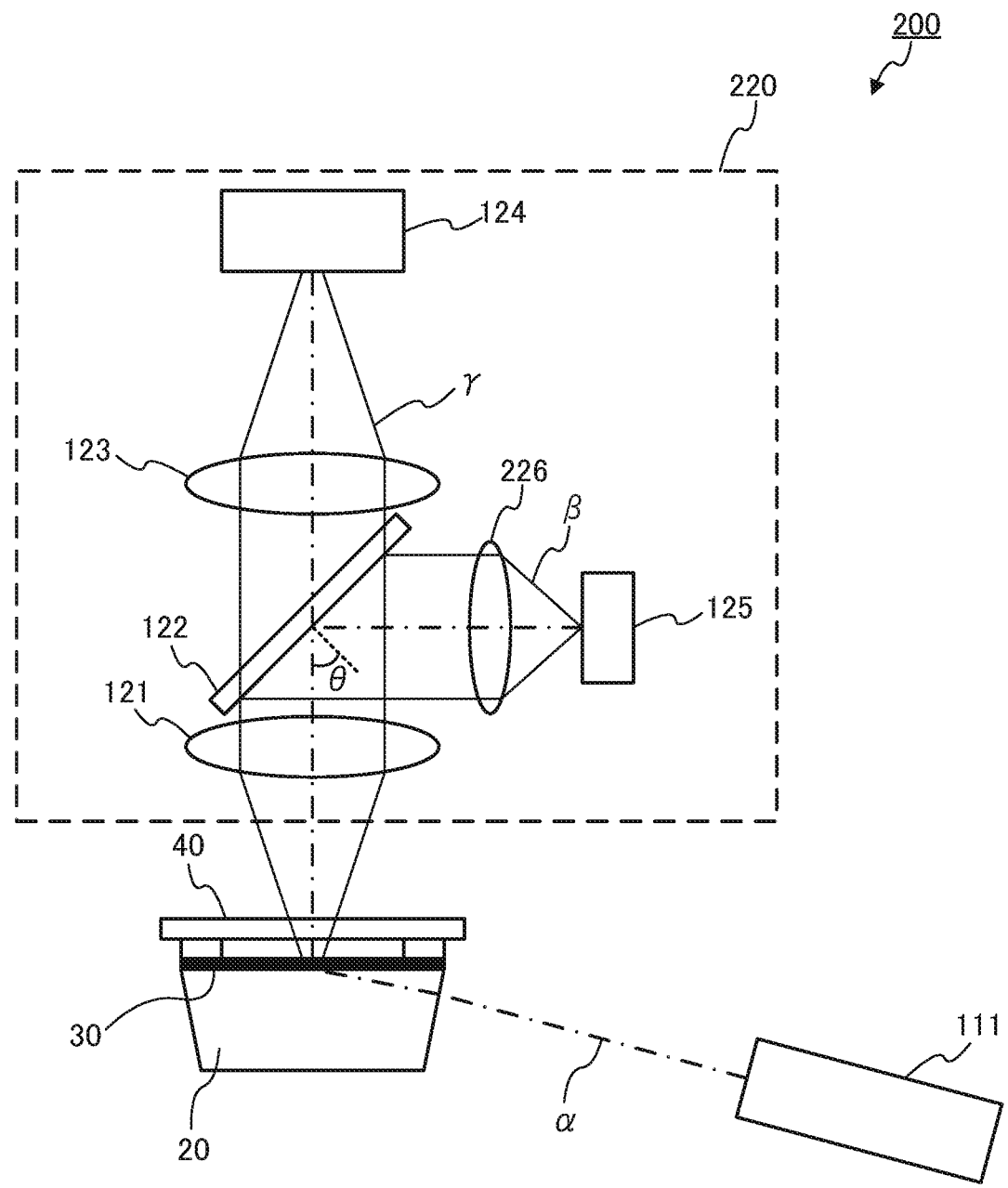
FIG. 4 is a partially enlarged schematic view of a surface plasmon resonance fluorescence analysis device according to Embodiment 2.

FIG. 4 is a partially enlarged schematic view of SPFS device 200 according to Embodiment 2. As illustrated in FIG. 4, light reception optical system unit 220 includes first lens 121, excitation light reflection filter 122, second lens 123, third lens 226, first light sensor 124 and second light sensor 125. First lens 121, second lens 123 and first light sensor 124 of light reception optical system unit 220 according to Embodiment 2 are identical to first lens 121, second lens 123 and first light sensor 124 of light reception optical system unit 120 according to Embodiment 1, respectively.

In the present embodiment, excitation light reflection filter 122 is disposed to be tilted by 45 degrees with respect to the optical axis of a conjugate optical system (light reception optical system) composed of first lens 121 and second lens 123. Accordingly, plasmon scattering light β is reflected by excitation light reflection filter 122 in a direction perpendicular to the optical axis of the conjugate optical system (light reception optical system).

Third lens 226 and second light sensor 125 are disposed on the side surface of a lens barrel (not shown in the drawing) that holds first lens 121 and second lens 123. Third lens 226 condenses plasmon scattering light β reflected by excitation light reflection filter 122 at the light reception surface of second light sensor 125. It is to be noted that when the intensity of plasmon scattering light β is sufficiently high, third lens 226 may not be disposed. In this case, second light sensor 125 detects part of plasmon scattering light β.

SPFS device 200 according to the present embodiment achieves an effect similar to that of SPFS device 100 according to Embodiment 1.

While the incident angle excitation optical system unit 110 is rotated with respect to analysis chip 10 at the time of scanning in the embodiments, analysis chip 10 may be rotated with respect to excitation optical system unit 110. In this case, the fluorescence image on metal film 30 is also tilted along with the rotation of analysis chip 10, but the variation of the light amount of the received light is negligible since the angle of the fluorescence image is several degrees and fluorescence γ is uniformly emitted from the fluorescence material in all 360 degrees.

This application is entitled to and claims the benefit of Japanese Patent Application No. 2013-149311 filed on Jul. 18, 2013, the disclosure of which including the specification, drawings and abstract is incorporated herein by reference in its entirety.

INDUSTRIAL APPLICABILITY

The surface plasmon resonance fluorescence analysis device and the surface plasmon resonance fluorescence analysis method according to the present invention can measure a substance to be detected with high reliability, and therefore are suitable for laboratory tests and the like, for example.

REFERENCE SIGNS LIST

10 Analysis chip
20 Prism
21 Incidence surface
22 Film formation surface
23 Emission surface
30 Metal film
40 Channel closure
41 Channel
100, 200 Surface plasmon resonance fluorescence analysis device
110 Excitation optical system unit
111 Light source unit
112 Angle adjusting section
120, 220 Light reception optical system unit
121 First lens
122 Excitation light reflection filter
123 Second lens
124 First light sensor
125 Second light sensor
130 Control section
131 Light source control section
132 First light sensor control section
133 Second light sensor control section
134 Control processing section
226 Third lens

The invention claimed is:

1. A surface plasmon resonance fluorescence analysis device to which an analysis chip including a prism having a metal film provided on one surface of the prism is attached, and in which the metal film is irradiated with excitation light through the prism to excite a fluorescence material for labelling a substance to be detected on the metal film and fluorescence emitted from the fluorescence material is detected to detect presence or an amount of the substance to be detected, the surface plasmon resonance fluorescence analysis device comprising:

a chip holder configured to detachably hold the analysis chip;

a light source configured to emit excitation light;

an angle adjusting section configured to adjust an incident angle of the excitation light with respect to the metal film to irradiate the metal film with the excitation light through the prism at a predetermined incident angle;

a first light sensor configured to detect fluorescence emitted from the fluorescence material;

a light reception optical system configured to guide light emitted from the metal film to the first light sensor;

an excitation light reflection filter disposed in the light reception optical system, and configured to reflect light having a wavelength same as that of the excitation light emitted from the light source in the light emitted from the metal film;

a second light sensor configured to detect the light reflected by the excitation light reflection filter; and a control section configured to control the angle adjusting section; wherein the control section controls the incident angle of the excitation light with respect to the metal film to be adjusted by the angle adjusting section on a basis of a detection result of the light obtained by the second light sensor.

2. The surface plasmon resonance fluorescence analysis device according to claim 1, wherein the excitation light reflection filter is disposed to be tilted with respect to an optical axis of the light reception optical system.

3. The surface plasmon resonance fluorescence analysis device according to claim 1, wherein an inclination angle θ(°) of a perpendicular of the excitation light reflection filter with respect to an optical axis of the light reception optical system satisfies Expression (1)

$$\tfrac{1}{2}\tan^{-1}(b/a) < \theta \leq 45 \tag{1}$$

wherein "a" is a distance between an intersection A of the optical axis with the excitation light reflection filter and an intersection B of the optical axis with the surface of the prism on which the metal film is provided; and "b" is a shortest distance to an end portion of the analysis chip from the intersection B in a direction orthogonal to the optical axis.

4. The surface plasmon resonance fluorescence analysis device according to claim 1, wherein the light reception optical system includes a first lens and a second lens;

the first lens, the excitation light reflection filter and the second lens are disposed in this order from a side of the metal film; and the second light sensor detects light reflected by the excitation light reflection filter and condensed by the first lens.

5. The surface plasmon resonance fluorescence analysis device according to claim 1, wherein the control section controls the light source such that a light amount of the excitation light is different between a state where the second light sensor detects light to determine the incident angle of the excitation light with respect to the metal film, and a state where the first light sensor detects light to detect the fluorescence emitted from the fluorescence material.

6. The surface plasmon resonance fluorescence analysis device according to claim 2, wherein an inclination angle θ(°) of a perpendicular of the excitation light reflection filter with respect to the optical axis of the light reception optical system satisfies Expression (1)

$$\tfrac{1}{2}\tan^{-1}(b/a) < \theta \leq 45 \tag{1}$$

wherein "a" is a distance between an intersection A of the optical axis with the excitation light reflection filter and an intersection B of the optical axis with the surface of the prism on which the metal film is provided; and "b" is a shortest distance to an end portion of the analysis chip from the intersection B in a direction orthogonal to the optical axis.

7. The surface plasmon resonance fluorescence analysis device according to claim 2, wherein the light reception optical system includes a first lens and a second lens;

the first lens, the excitation light reflection filter and the second lens are disposed in this order from a side of the metal film; and the second light sensor detects light reflected by the excitation light reflection filter and condensed by the first lens.

8. The surface plasmon resonance fluorescence analysis device according to claim 3, wherein the light reception optical system includes a first lens and a second lens;

the first lens, the excitation light reflection filter and the second lens are disposed in this order from a side of the metal film; and the second light sensor detects light reflected by the excitation light reflection filter and condensed by the first lens.

9. The surface plasmon resonance fluorescence analysis device according to claim 5, wherein the control section controls the light source such that a light amount of the excitation light at a time when the second light sensor detects light to determine the incident angle of the excitation light with respect to the metal film is greater than a light amount of the excitation light at a time when the first light sensor detects light to detect the fluorescence emitted from the fluorescence material.

10. The surface plasmon resonance fluorescence analysis device according to claim 6, wherein the light reception optical system includes a first lens and a second lens;

the first lens, the excitation light reflection filter and the second lens are disposed in this order from a side of the metal film; and the second light sensor detects light reflected by the excitation light reflection filter and condensed by the first lens.

11. A surface plasmon resonance fluorescence analysis method in which fluorescence which is emitted by a fluorescence material for labelling a substance to be detected when the fluorescence material is excited by localized-field light based on surface plasmon resonance is detected to detect presence or an amount of the substance to be detected, the surface plasmon resonance fluorescence analysis method comprising:

providing the surface plasmon resonance fluorescence analysis device according to claim 1, determining a reinforcement angle which is an incident angle at which an intensity of plasmon scattering light emitted from the metal film and reflected by the excitation light reflection filter is maximized, by irradiating the metal film with the excitation light through the prism while changing the incident angle with respect to the metal film by the angle adjusting section, and by detecting the intensity of the plasmon scattering light by the second light sensor, the metal film being provided on the one surface of the prism;

placing the substance to be detected which is labeled by the fluorescence material on the metal film; and detecting an intensity of fluorescence light by the first light sensor wherein the fluorescence light is emitted from the fluorescence material for labelling the substance to be detected, and transmitted through the excitation light reflection filter, by irradiating the metal film with the excitation light through the prism such that the incident angle with respect to the metal film is the reinforcement angle.

12. The surface plasmon resonance fluorescence analysis method according to claim 11, wherein, in the determining of the reinforcement angle which is the incident angle at which the intensity of the plasmon scattering light is maximized, a light amount of the excitation light is different between a state where the second light sensor detects light to determine the incident angle of the excitation light with respect to the metal film, and a state where the first light sensor detects light to detect the fluorescence emitted from the fluorescence material.

13. The surface plasmon resonance fluorescence analysis method according to claim 12, wherein a light amount of the excitation light at a time when the plasmon scattering light is detected is greater than a light amount of the excitation light at a time when the fluorescence is detected.

* * * * *